US012620095B2

(12) United States Patent
Shiraishi

(10) Patent No.: US 12,620,095 B2
(45) Date of Patent: May 5, 2026

(54) CELL QUALITY EVALUATION APPARATUS, CELL QUALITY EVALUATION METHOD, AND PROGRAM

(71) Applicant: FUJIFILM CORPORATION, Tokyo (JP)

(72) Inventor: Yasushi Shiraishi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 283 days.

(21) Appl. No.: 18/534,723

(22) Filed: Dec. 11, 2023

(65) Prior Publication Data

US 2024/0153083 A1     May 9, 2024

Related U.S. Application Data

(63) Continuation of application No. PCT/JP2022/021564, filed on May 26, 2022.

(30) Foreign Application Priority Data

Jun. 24, 2021     (JP) ................................ 2021-104816

(51) Int. Cl.
*G06T 7/00*          (2017.01)
*C12M 1/34*          (2006.01)
(Continued)

(52) U.S. Cl.
CPC ........... *G06T 7/0012* (2013.01); *C12M 41/36* (2013.01); *C12M 41/46* (2013.01); *C12M 41/48* (2013.01);
(Continued)

(58) Field of Classification Search
CPC ......... G06T 7/0012; G06T 2207/10056; G06T 2207/20216; G06T 2207/30024;
(Continued)

(56) References Cited

U.S. PATENT DOCUMENTS

2009/0304257 A1     12/2009  Ohjo et al.
2010/0208960 A1*     8/2010  Kiyota ................... C12M 41/48
                                                            382/128

(Continued)

FOREIGN PATENT DOCUMENTS

JP          2007-275030 A       10/2007
JP          2011-229409 A       11/2011
(Continued)

OTHER PUBLICATIONS

Auld, Douglas S., et al. "Microplate selection and recommended practices in high-throughput screening and quantitative biology." Assay Guidance Manual [Internet] (2020). (Year: 2020).*

(Continued)

*Primary Examiner* — Sumati Lefkowitz
*Assistant Examiner* — Ryan P Potts
(74) *Attorney, Agent, or Firm* — SOLARIS Intellectual

(57)          ABSTRACT

A cell quality evaluation apparatus performs a process including estimation processing of estimating a quality of cells in the entirety of a cell-culture container by determining feature quantities from a plurality of images and calculating an average value of the feature quantities; derivation processing of deriving an estimation error of the quality estimated in the estimation processing, based on a variation of the feature quantities in the plurality of images and imaging information related to an area of a plurality of imaging regions; and imaging control processing of causing a imaging apparatus to perform re-imaging on at least one re-imaging region different from the plurality of imaging regions in a case where the estimation error is out of an allowable range.

8 Claims, 14 Drawing Sheets

(51) Int. Cl.

| | |
|---|---|
| *C12M 1/36* | (2006.01) |
| *G01N 33/483* | (2006.01) |
| *G06V 20/69* | (2022.01) |
| *G16H 10/40* | (2018.01) |
| *H04N 23/60* | (2023.01) |

(52) U.S. Cl.

CPC ......... *G01N 33/483* (2013.01); *G06V 20/695* (2022.01); *G16H 10/40* (2018.01); *H04N 23/64* (2023.01); *G06T 2207/10056* (2013.01); *G06T 2207/20216* (2013.01); *G06T 2207/30024* (2013.01); *G06T 2207/30168* (2013.01)

(58) Field of Classification Search

CPC ......... G06T 2207/30168; C12M 41/36; C12M 41/46; C12M 41/48; G01N 33/483; G06V 20/695; G16H 10/40; H04N 23/64

See application file for complete search history.

(56) References Cited

U.S. PATENT DOCUMENTS

| | | | |
|---|---|---|---|
| 2013/0194410 A1* | 8/2013 | Topman .................. | G06V 20/69 |
| | | | 382/133 |
| 2015/0086102 A1 | 3/2015 | Fujimoto et al. | |
| 2017/0204359 A1* | 7/2017 | Ando ...................... | C12M 41/36 |
| 2020/0110923 A1 | 4/2020 | Tanikawa et al. | |
| 2022/0284719 A1* | 9/2022 | Amthor ..................... | G06T 3/40 |

FOREIGN PATENT DOCUMENTS

| | | | | | |
|---|---|---|---|---|---|
| JP | 2011-229411 A | 11/2011 | | | |
| JP | 2015-065812 A | 4/2015 | | | |
| JP | 5740102 B2 | 6/2015 | | | |
| WO | WO-2015107667 A1 * | 7/2015 | ........... | C12M 41/36 |
| WO | 2016/098271 A1 | 6/2016 | | | |
| WO | 2018/229920 A1 | 12/2018 | | | |
| WO | 2019/225325 A1 | 11/2019 | | | |

OTHER PUBLICATIONS

Baradez, Marc-Olivier, and Damian Marshall. "The use of multi-dimensional image-based analysis to accurately monitor cell growth in 3D bioreactor culture." PLoS One 6.10 (2011): e26104. (Year: 2011).*

Ryan, John A. "Corning guide for identifying and correcting common cell growth problems." Corning Incorporated (2012). (Year: 2012).*

Jaccard, Nicolas, et al. "Automated method for the rapid and precise estimation of adherent cell culture characteristics from phase contrast microscopy images." Biotechnology and bioengineering 111.3 (2014): 504-517. (Year: 2014).*

Ker, Dai Fei Elmer, et al. "An engineered approach to stem cell culture: automating the decision process for real-time adaptive subculture of stem cells." PLoS One 6.11 (2011): e27672. (Year: 2011).*

Kofron, Celinda M., and Diane Hoffman-Kim. "Optimization by response surface methodology of confluent and aligned cellular monolayers for nerve guidance." Cellular and molecular bioengineering 2.4 (2009): 554-572. (Year: 2009).*

Extended European Search Report dated Sep. 30, 2024, issued in corresponding EP Patent Application No. 22828139.0.

International Search Report issued in International Application No. PCT/JP2022/021564 on Aug. 9, 2022.

Written Opinion of the ISA issued in International Application No. PCT/JP2022/021564 on Aug. 9, 2022.

* cited by examiner

FIG. 6

FIRST SEEDING METHOD ⁓P

SECOND SEEDING METHOD ⁓P

FIG. 15

| AREA RATIO N/M | ESTIMATION ERROR |
|:---:|:---:|
| ... | ... |
| ... | ... |
| ... | ... |

~T

CELL QUALITY EVALUATION APPARATUS, CELL QUALITY EVALUATION METHOD, AND PROGRAM

CROSS-REFERENCE TO RELATED APPLICATIONS

This application is a continuation application of International Application No. PCT/JP2022/021564, filed May 26, 2022, the disclosure of which is incorporated herein by reference in its entirety. Further, this application claims priority from Japanese Patent Application No. 2021-104816, filed on Jun. 24, 2021, the disclosure of which is incorporated herein by reference in its entirety.

BACKGROUND

1. Technical Field

The technique of the present disclosure relates to a cell quality evaluation apparatus, a cell quality evaluation method, and a program.

2. Description of the Related Art

In the fields of regenerative medicine, new drug development, and the like, there is known a technique for evaluating the quality of cells that are being cultured in a cell-culture container, by analyzing captured images obtained by imaging the cell-culture container with an imaging apparatus such as a microscope (for example, see WO2016/098271A).

WO2016/098271A discloses calculating a proportion of a cell-occupied area (hereinafter, referred to as confluency) which is a proportion of an area occupied by cells in a cell-culture container on the basis of a plurality of images acquired from a plurality of measurement areas (imaging regions) designated in the cell-culture container. Confluency is one indicator representing the quality of cells that are being cultured.

SUMMARY

In the case where the quality of cells is estimated on the basis of images acquired from a plurality of imaging regions selected from the entire cell-culture container as described in WO2016/098271A, an estimation error of the quality depends on the number and the size of the imaging regions selected from the entire cell-culture container. To reduce the estimation error of the quality, the entire cell-culture container needs to be imaged by increasing the number of imaging regions selected from the entire cell-culture container or by increasing the area of the imaging regions.

Imaging the entire cell-culture container is possible when the cell-culture container has a small volume such as wells in a well plate but is difficult when the cell-culture container has a large volume such as a T-flask. Microscopes capable of imaging the entire large-volume cell-culture container are present. However, such microscopes are large costly apparatuses and thus are difficult for ordinary users to introduce and operate. Accordingly, development of a cell quality evaluation apparatus that allows the quality of cells to be evaluated with a high accuracy even for a large-volume cell-culture container is desired.

The technique of the present disclosure aims to provide a cell quality evaluation apparatus, a cell quality evaluation method, and a program that allow the quality of cells to be evaluated with a high accuracy even for a large-volume cell-culture container.

A cell quality evaluation apparatus according to the present disclosure is a cell quality evaluation apparatus that evaluates a quality of cells based on a plurality of images acquired from an imaging apparatus that generates the plurality of images by imaging a plurality of imaging regions selected from entirety of a cell-culture container for culturing cells. The cell quality evaluation apparatus includes at least one processor configured to perform a process including estimation processing of estimating a quality of cells in the entirety of the cell-culture container by determining feature quantities from the plurality of images and calculating an average value of the feature quantities; derivation processing of deriving an estimation error of the quality estimated in the estimation processing, based on a variation of the feature quantities in the plurality of images and imaging information related to an area of the plurality of imaging regions; and imaging control processing of causing the imaging apparatus to perform re-imaging on at least one re-imaging region different from the plurality of imaging regions in a case where the estimation error is out of an allowable range.

Preferably, the imaging information is a number of images that are the plurality of images, and the estimation error is represented by $\sigma/N^{1/2}$, where $\sigma$ denotes a standard deviation that is the variation of the feature quantities and N denotes the number of images.

Preferably, in the imaging control processing, the re-imaging region is set based on the variation of the feature quantities and position information of the plurality of imaging regions.

Preferably, in the imaging control processing, the re-imaging region is set based on a surface shape of the cell-culture container.

Preferably, the feature quantities are proportions of a cell-occupied area, areas of cell nuclei, or area ratios between cell nuclei and cytoplasm.

Preferably, the feature quantities are proportions of a cell-occupied area, and in the imaging control processing, the imaging apparatus is caused to perform re-imaging more in a region with a proportion of a cell-occupied area of about 50% than in other regions.

Preferably, in the derivation processing, the estimation error is derived based on a table that defines a relationship between the estimation error and a ratio of an area of already imaged imaging regions to the entirety of the cell-culture container.

A cell quality evaluation method according to the present disclosure is a cell quality evaluation method for evaluating a quality of cells based on a plurality of images acquired from an imaging apparatus that generates the plurality of images by imaging a plurality of imaging regions selected from entirety of a cell-culture container for culturing cells. The cell quality evaluation method includes performing a process including: estimation processing of estimating a quality of cells in the entirety of the cell-culture container by determining feature quantities from the plurality of images and calculating an average value of the feature quantities; derivation processing of deriving an estimation error of the quality estimated in the estimation processing, based on a variation of the feature quantities in the plurality of images and imaging information related to an area of the plurality of imaging regions; and imaging control processing of causing the imaging apparatus to perform re-imaging on at least one re-imaging region different from the plurality of imaging regions in a case where the estimation error is out of an allowable range.

A program according to the present disclosure is a program for causing a computer to execute a process for evaluating a quality of cells based on a plurality of images acquired from an imaging apparatus that generates the plurality of images by imaging a plurality of imaging regions selected from entirety of a cell-culture container for culturing cells. The process includes estimation processing of estimating a quality of cells in the entirety of the cell-culture container by determining feature quantities from the plurality of images and calculating an average value of the feature quantities; derivation processing of deriving an estimation error of the quality estimated in the estimation processing, based on a variation of the feature quantities in the plurality of images and imaging information related to an area of the plurality of imaging regions; and imaging control processing of causing the imaging apparatus to perform re-imaging on at least one re-imaging region different from the plurality of imaging regions in a case where the estimation error is out of an allowable range.

The technique of the present disclosure can provide a cell quality evaluation apparatus, a cell quality evaluation method, and a program that allow the quality of cells to be evaluated with a high accuracy even for a large-volume cell-culture container.

BRIEF DESCRIPTION OF THE DRAWINGS

Exemplary embodiments according to the technique of the present disclosure will be described in detail based on the following figures, wherein:

FIG. 6 is a schematic diagram illustrating an example of quality estimation processing performed by a quality estimation unit;

FIG. 12A illustrates an example of an image obtained in the case where cells are seeded using the first seeding method and FIG. 12B illustrates an example of an image obtained in the case where cells are seeded using the second seeding method;

FIG. 15 is a diagram illustrating an example of a table for deriving the estimation error.

DETAILED DESCRIPTION

An example of an embodiment according to the technique of the present disclosure will be described with reference to the accompanying drawings.

Figure 1:
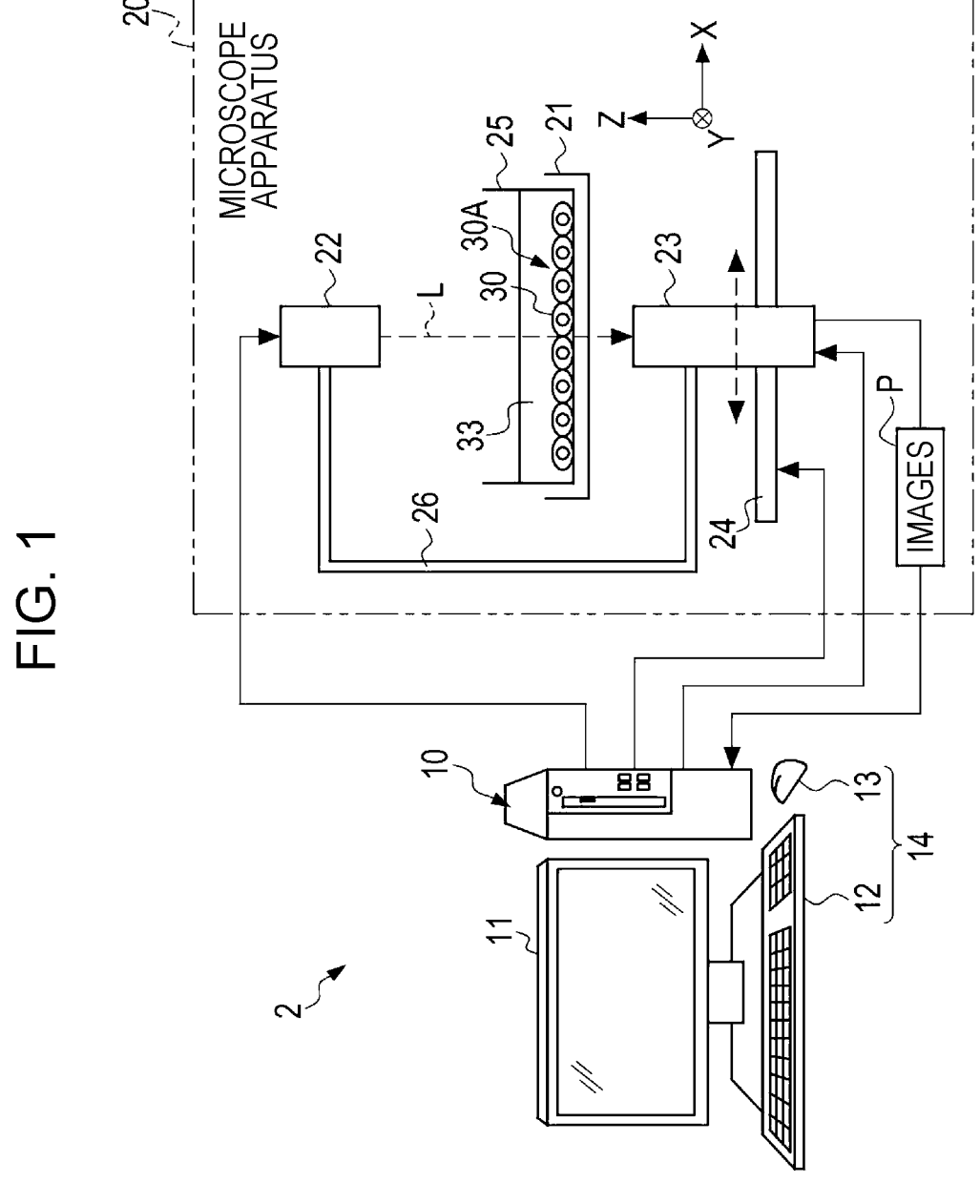
FIG. 1 is a schematic diagram illustrating an example of a configuration of a microscope observation system.

As illustrated in FIG. 1 as an example, a microscope observation system 2 is constituted by an information processing apparatus 10 and a microscope apparatus 20. The information processing apparatus 10 is, for example, a desktop personal computer. A display 11, a keyboard 12, a mouse 13, and the like are connected to the information processing apparatus 10. The keyboard 12 and the mouse 13 constitute an input device 14 with which a user inputs information. The input device 14 includes a touch panel or the like. The information processing apparatus 10 is an example of a "cell quality evaluation apparatus" according to the technique of the present disclosure.

The microscope apparatus 20 includes a mount 21, a light source 22, an imaging apparatus 23, and a driving unit 24. The microscope apparatus 20 is a phase contrast microscope or a bright field microscope. A cell-culture container 25 for culturing cells 30 is mounted on the mount 21. The cell-culture container 25 is, for example, a T-flask. The T-flask is an example of a large-volume cell-culture container. The cells 30 are cultured using a culture medium 33 that fills the cell-culture container 25. For example, the cells 30 are pluripotent stem cells in an undifferentiated state, such as induced pluripotent stem (iPS) cells or embryonic stem (ES) cells. Note that the cell-culture container 25 is not limited to a flask such as a T-flask, and may be a petri dish, a cell-culture dish, a well plate, or the like.

The light source 22 and the imaging apparatus 23 are held by an arm 26. The mount 21 is disposed between the light source 22 and the imaging apparatus 23. Specifically, the light source 22 is disposed above the cell-culture container 25 mounted on the mount 21. The imaging apparatus 23 is disposed at a position below the mount 21 to face the light source 22. The light source 22 emits illumination light L toward the cell-culture container 25. Hereinafter, an emission direction of the illumination light L is referred to as a "Z direction", one direction orthogonal to the Z direction is referred to as an "X direction", and a direction orthogonal to the Z direction and the X direction is referred to as a "Y direction". The imaging apparatus 23 is, for example, a complementary metal-oxide semiconductor (CMOS) image sensor. The imaging apparatus 23 may be an image sensor provided with color filters or may be a monochrome image sensor. In addition to the image sensor, the imaging apparatus 23 is provided with an optical system (not illustrated) including an objective lens. The imaging apparatus 23 images a plurality of imaging regions selected from the entirety of the cell-culture container 25.

The imaging apparatus 23 images, for each of the imaging regions, the plurality of cells 30 (also referred to as a cell population 30A) irradiated with the illumination light L by the light sources 22, and outputs a captured image obtained as a result of the imaging as an image P to the information processing apparatus 10.

The driving unit 24 is connected to the imaging apparatus 23 and moves the imaging apparatus 23 in two-dimensional directions. The light source 22 moves in conjunction with movement of the imaging apparatus 23. For example, the driving unit 24 is an XY stage that moves the imaging apparatus 23 in the X direction and the Y direction.

Figure 2:
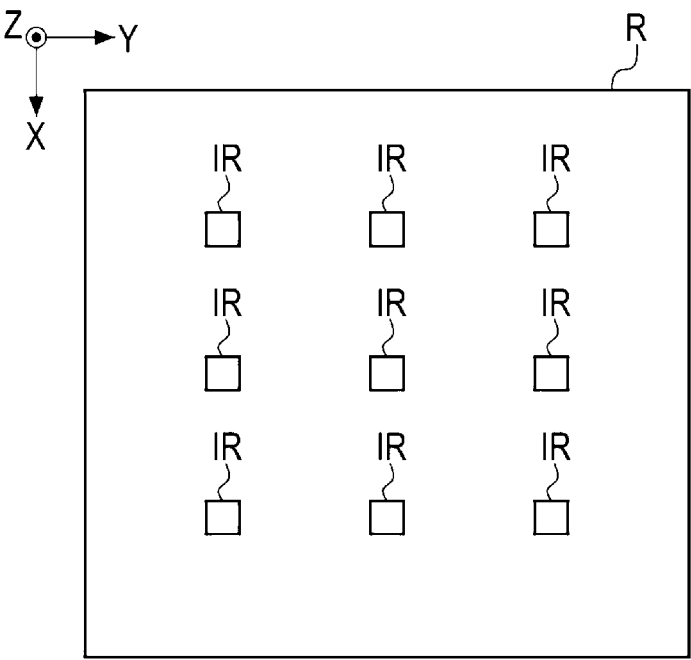
FIG. 2 is a schematic diagram illustrating an example of a plurality of imaging regions set in a culture region.

The information processing apparatus 10 integrally controls operations of the light source 22, the imaging apparatus 23, and the driving unit 24. As illustrated in FIG. 2 as an example, the information processing apparatus 10 sets a plurality of imaging regions IR in a culture region R corresponding to the entirety of cell-culture container 25 (i.e., entirety of a cell adhesion surface), and controls the driving unit 24 to cause the imaging apparatus 23 to image the cell population 30A in each of the imaging regions IR. The imaging regions IR are regions imaged by the imaging apparatus 23 in one imaging operation.

In the case where the cell-culture container 25 is a T-flask, the culture region R has an area of about 25 cm², for example. The imaging regions IR each have an area of about 4 mm², for example. The area of each imaging region IR depends on an imaging magnification of the optical system and the size of the image sensor of the imaging apparatus 23. The area of each imaging region IR is inversely proportional to a square of the imaging magnification. For example, changing the imaging magnification from 10 times to 4 times implements a 6.25-fold increase in the area of the imaging region IR.

Figure 3:
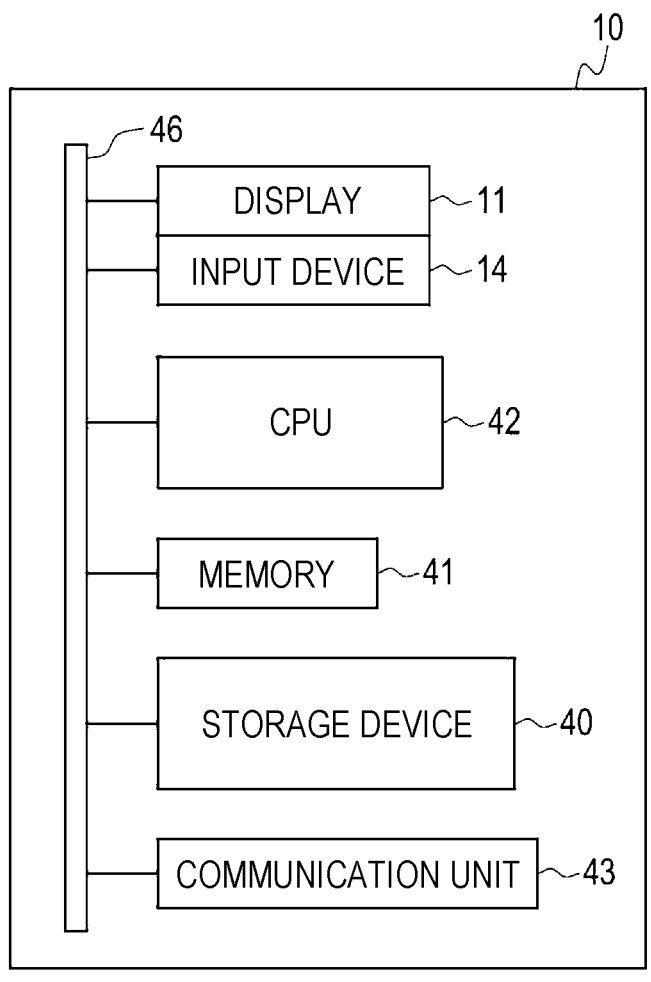
FIG. 3 is a block diagram illustrating an example of an internal configuration of an information processing apparatus.

As illustrated in FIG. 3 as an example, a computer constituting the information processing apparatus 10 includes a storage device 40, a memory 41, a central processing unit (CPU) 42, a communication unit 43, the display 11, and the input device 14. These components are connected to one another through a bus line 46.

The storage device 40 is a hard disk drive built in the computer constituting the information processing apparatus 10 or connected to the computer by a cable or via a network. The storage device 40 may also be a disk array that is a plurality of hard disk drives connected to one another. The storage device 40 stores a control program such as an operating system, various application programs, various kinds of data for these programs, and so on. Note that a solid state drive may be used instead of the hard disk drive.

The memory 41 is a work memory used by the CPU 42 to execute a process. The CPU 42 loads a program stored in the storage device 40 into the memory 41 and executes a process in accordance with the program to integrally control each component of the computer.

The communication unit 43 is a network interface that controls transmission of various kinds of information via a network such as a local area network (LAN). The display 11 displays various screens. The computer constituting the information processing apparatus 10 receives an input of an operation instruction from the input device 14 via the various screens.

The information processing apparatus 10 estimates the quality of the cell population 30A on the basis of the plurality of images P generated as a result of the imaging apparatus 23 imaging the plurality of imaging regions IR selected from the entirety of the cell-culture container 25, and causes the imaging apparatus 23 to perform re-imaging if an estimation error is out of an allowable range. An imaging region to be imaged by re-imaging is a region different from the plurality of imaging regions IR.

Figure 4:
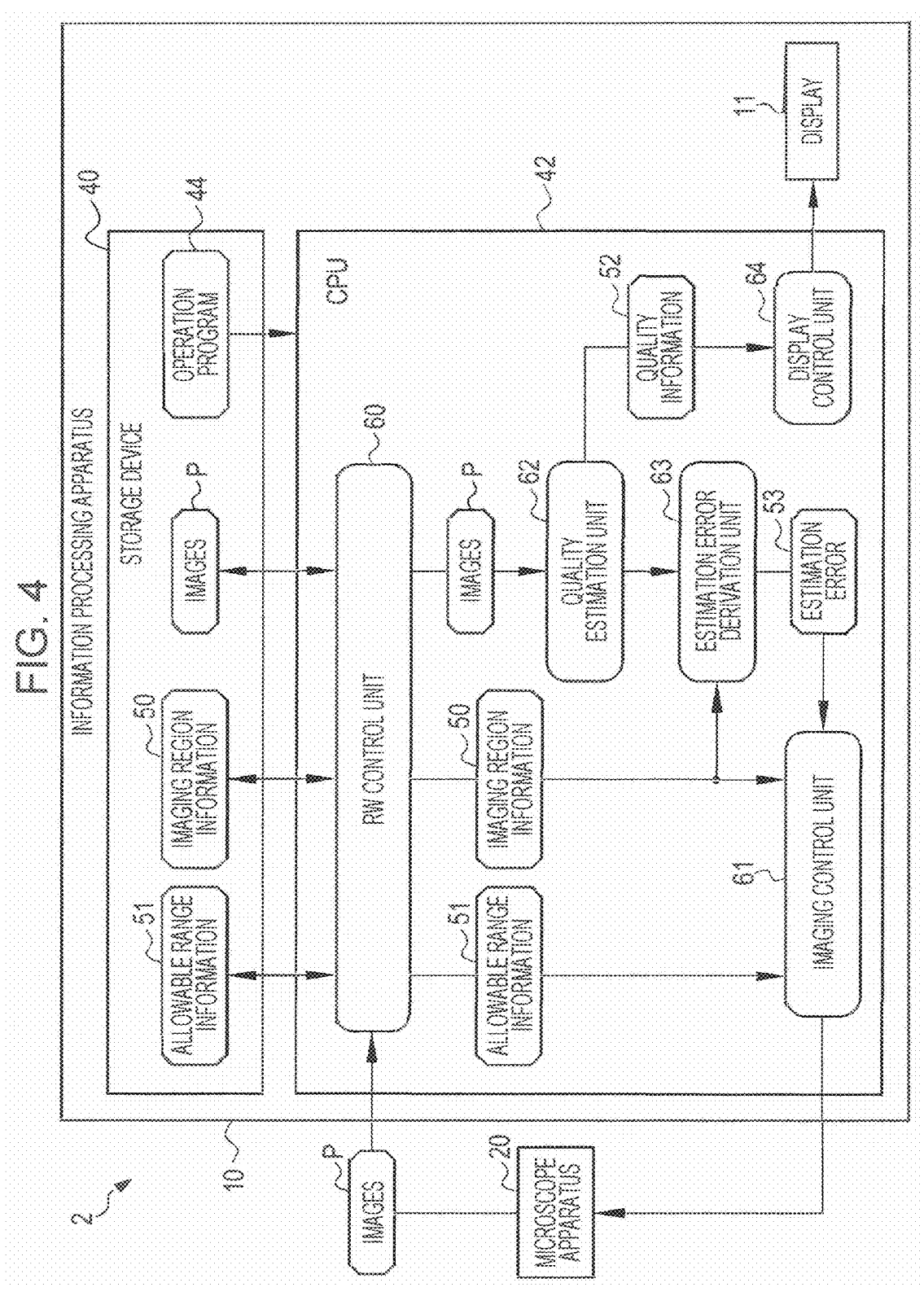
FIG. 4 is a block diagram illustrating an example of a functional configuration of the information processing apparatus.

As illustrated in FIG. 4 as an example, the storage device 40 of the information processing apparatus 10 stores an operation program 44. The operation program 44 is an application program for causing the computer to function as the information processing apparatus 10. That is, the operation program 44 is an example of a "program" according to the technique of the present disclosure.

In addition to the operation program 44, the storage device 40 stores imaging region information 50 and allowable range information 51. The storage device 40 also stores the plurality of images P input from the imaging apparatus 23. For example, the imaging region information 50 and the allowable range information 51 are input in advance by a user using the input device 14.

In response to the start of the operation program 44, the CPU 42 of the computer constituting the information processing apparatus 10 operates in cooperation with the memory 41 and the like to function as a read/write (hereinafter abbreviated as RW) control unit 60, an imaging control unit 61, a quality estimation unit 62, an estimation error derivation unit 63, and a display control unit 64.

The RW control unit 60 controls writing of various kinds of data to the storage device 40 and reading of various kinds of data from the storage device 40. For example, the RW control unit 60 receives the images P output from the imaging apparatus 23 of the microscope apparatus 20 and writes the images P in the storage device 40.

The imaging control unit 61 acquires the imaging region information 50 from the storage device 40 via the RW control unit 60, and causes the imaging apparatus 23 to perform an imaging operation on the basis of the acquired imaging region information 50. The imaging region information 50 includes position information of the plurality of imaging regions IR (see FIG. 2) and information indicating the number of imaging regions IR. The plurality of images P that are output from the imaging apparatus 23 as a result of the imaging apparatus 23 imaging the plurality of imaging regions IR are written in the storage device 40 via the RW control unit 60.

The quality estimation unit 62 acquires, via the RW control unit 60, the plurality of images P stored in the storage device 40, and performs estimation processing of estimating the quality of cells on the basis of the plurality of acquired images P. Specifically, the quality estimation unit 62 estimates the quality of cells in the entirety of the cell-culture container 25 by determining feature quantities F from the plurality of images P and calculating an average value of the feature quantities F. Here, the plurality of images P correspond to samples whose population is the entirety of the cell-culture container 25. The quality estimation unit 62 outputs the average value of the feature quantities F as quality information 52 to the display control unit 64.

In the present embodiment, the quality estimation unit 62 estimates confluency of the cell population 30A in the entire cell-culture container 25 by deriving confluency of the cell population 30A (a proportion of a cell-occupied area) as the feature quantity F and determining an average confluency value.

The estimation error derivation unit 63 performs derivation processing of deriving an estimation error 53 of the quality estimated by the quality estimation unit 62, on the basis of a variation of the feature quantities F in the plurality of images P and imaging information related to the area of the plurality of imaging regions IR. In the present embodiment, the imaging information related to the area of the plurality of imaging regions IR is the number of imaging regions IR included in the imaging region information 50 (i.e., the number of images P acquired by the imaging apparatus 23). This is because the area of the plurality of imaging regions IR is proportional to the number of imaging regions IR.

In the present embodiment, the estimation error derivation unit 63 derives a standard error SE on the basis of the variation (i.e., a standard deviation) of the feature quantities F determined by the quality estimation unit 62 and the number of images P (i.e., the number of samples). The estimation error derivation unit 63 outputs the derived standard error SE as the estimation error 53 to the imaging control unit 61.

The imaging control unit 61 acquires the allowable range information 51 from the storage device 40 via the RW control unit 60, and determines whether the estimation error 53 input from the estimation error derivation unit 63 is within an allowable range. The allowable range is a range in which the estimation error of the quality estimated by the quality estimation unit 62 is allowable, and is set by a user in advance, for example.

If the estimation error is out of the allowable range, the imaging control unit 61 performs imaging control processing of causing the imaging apparatus 23 to perform re-imaging on at least one re-imaging region different from the plurality of imaging regions. Information on the re-imaging region(s) is included in the imaging region information 50. The imaging control unit 61 sets one or more re-imaging regions in the culture region R on the basis of the imaging region information 50, and causes the imaging apparatus 23 to image the set re-imaging regions.

If re-imaging is performed by the imaging apparatus 23, the quality estimation unit 62 adds the image(s) P obtained by the re-imaging to the plurality of images P described above, and estimates the quality of cells in the entirety of the cell-culture container 25. After the quality estimation unit 62 estimates the quality again, the estimation error derivation unit 63 derives the estimation error 53 again.

If the imaging control unit 61 determines that the estimation error 53 is within the allowable range, the display control unit 64 causes the display 11 to display the quality information 52 output from the quality estimation unit 62.

Figure 5:
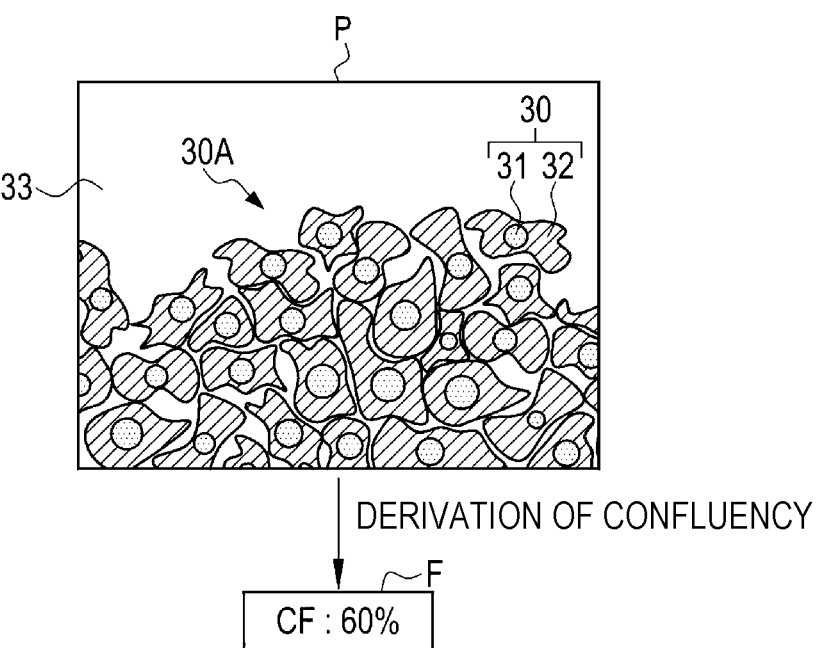
FIG. 5 is a schematic diagram illustrating an example of an image acquired by an imaging apparatus.

FIG. 5 is an example of the image P acquired by the imaging apparatus 23. As illustrated in FIG. 5, the cell population 30A constituted by the plurality of cells 30 is depicted in the image P. Each of the cells 30 includes a cell nucleus 31 and cytoplasm 32. A region other than the cells 30 in the image P is the culture medium 33.

The quality estimation unit 62 identifies the cells 30 from the image P by using a method based on image analysis or machine learning. The quality estimation unit 62 then determines an area ratio between the cells 30 and the culture medium 33 in the image P to derive confluency CF as the feature quantity F.

Figure 6:
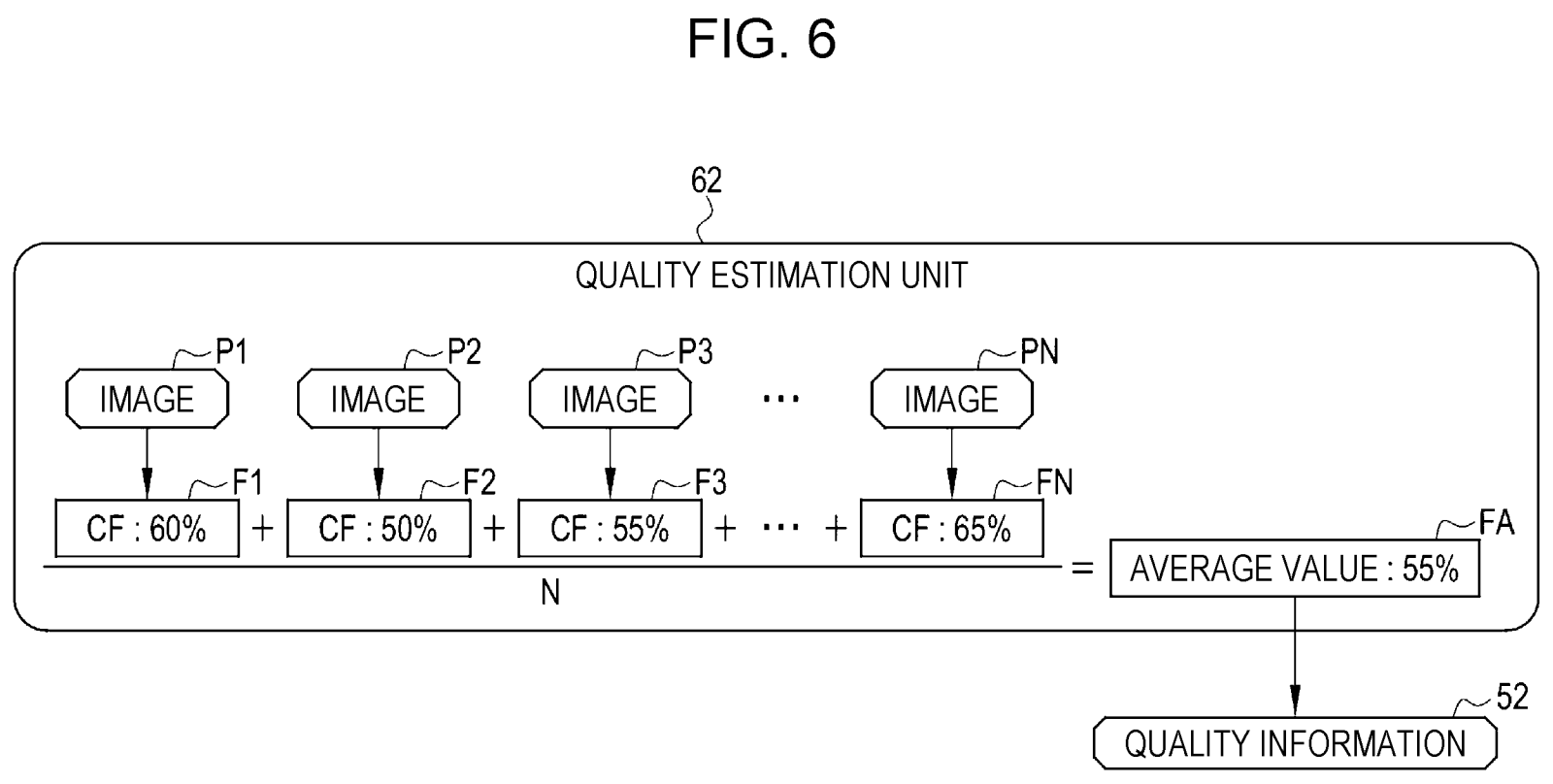

FIG. 6 illustrates an example of the quality estimation processing performed by the quality estimation unit 62. FIG. 6 illustrates a case where the number of images P acquired by the imaging apparatus 23, that is, the number of samples is N. In FIG. 6, images P1 to PN represent the N images P acquired by the imaging apparatus 23. Feature quantities F1 to FN represent the confluency CF derived from the respective images P1 to PN.

The quality estimation unit 62 calculates an average value FA of the feature quantities F1 to FN (i.e., the average value of the confluency CF), and outputs the average value FA as the quality information 52.

Figure 7:
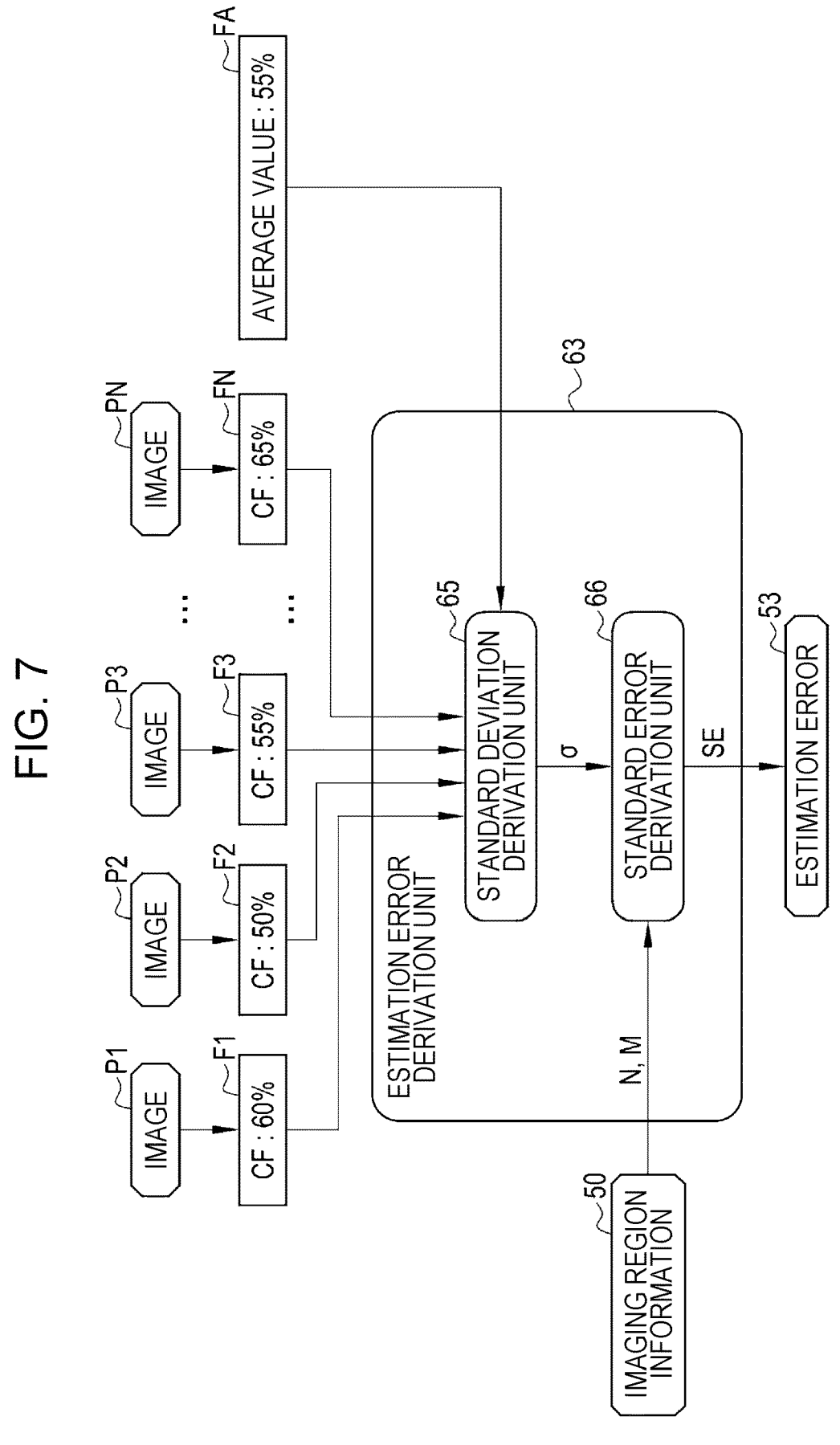
FIG. 7 is a schematic diagram illustrating an example of estimation error derivation/estimation processing performed by an estimation error derivation unit.

FIG. 7 illustrates an example of estimation error derivation/estimation processing performed by the estimation error derivation unit 63. The estimation error derivation unit 63 is constituted by, for example, a standard deviation derivation unit 65 and a standard error derivation unit 66. In the present embodiment, it is assumed that a distribution of the feature quantity F with respect to the entirety of the cell-culture container 25 (population) follows a normal distribution. It is also assumed that a distribution of the average value FA (sample mean) of the feature quantities F for the respective images P1 to PN approaches the normal distribution (i.e., follows the central limit theorem) as the number of samples N increases.

For example, the standard deviation derivation unit 65 derives a standard deviation σ indicating a variation of the feature quantities F on the basis of Expression (1) below. Here, N represents the number of images P (the number of samples). Fi represents a feature quantity Fi of an image Pi. FA represents the average value of the feature quantities F1 to FN.

$$\sigma = \sqrt{\frac{1}{N-1} \sum_{i=1}^{N} (Fi - FA)^2} \tag{1}$$

For example, the standard error derivation unit 66 derives a standard error SE on the basis of Expression (2) below. Here, σ represents the standard deviation derived by the standard deviation derivation unit 65. N represents the number of images P (the number of samples). M represents the number of elements of the population, that is, the number of imaging regions IR needed when the entirety of the cell-culture container 25 is captured. In Expression (2) below, N/M represents a ratio of an area of the already imaged imaging regions IR to the entirety of the cell-culture container 25 (the culture region R). Note that the already imaged imaging regions IR also include the re-imaging region that has been subjected to re-imaging. The imaging region information 50 described above also includes the number of elements M of the population.

$$SE = \sqrt{1 - \frac{N}{M}} \frac{\sigma}{\sqrt{N}} \tag{2}$$

The standard error SE represents a standard deviation (i.e., a standard deviation of the sample mean) of the estimated value (the average value FA of the feature quantities F) of the quality estimated by the quality estimation unit 62. Expression (2) above indicates that as the number N of images P increases, the standard error SE decreases and an estimation accuracy of the quality estimated by the quality estimation unit 62 increases. Expression (2) above also indicates that as the ratio of the area of the plurality of imaging regions to the entirety of the cell-culture container 25 increases (i.e., as the value of an area ratio N/M approaches 1), the standard error SE decreases.

When the number of elements M of the population is sufficiently large relative to the number N of images P, the quality estimation unit 62 may derive the standard error SE by using Expression (3) below instead of Expression (2) above.

$$SE = \frac{\sigma}{\sqrt{N}} \tag{3}$$

Figure 8:
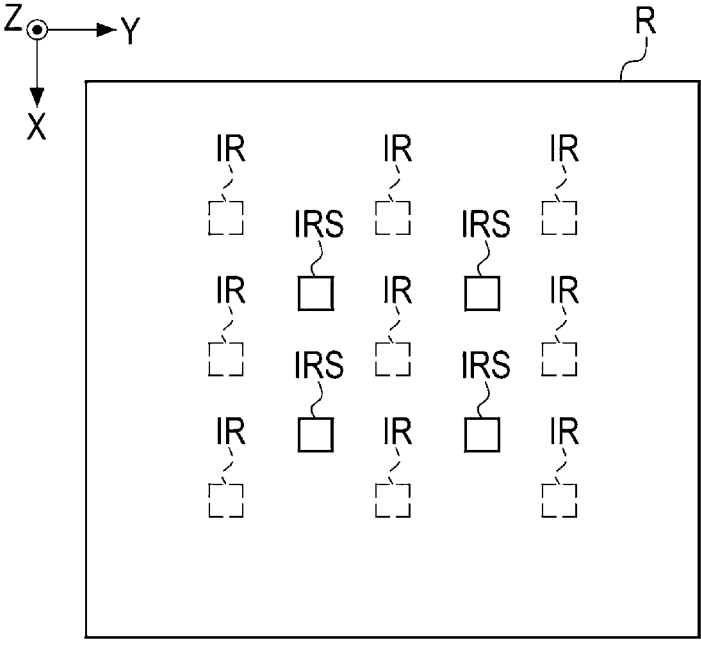
FIG. 8 is a schematic diagram illustrating an example of re-imaging regions set by an imaging control unit.

FIG. 8 illustrates an example of re-imaging regions IRS set by the imaging control unit 61. The re-imaging regions IRS have the same shape and the same size as the imaging regions IR. As illustrated in FIG. 8, for example, the re-imaging regions IRS are set at positions different in the X direction and the Y direction from the already imaged imaging regions IR in the culture region R.

A cell quality evaluation process performed by the information processing apparatus 10 will be described next with reference to a flowchart illustrated in FIG. 9 as an example. First, in the information processing apparatus 10, the CPU 42 executes a process on the basis of the operation program 44, so that the CPU 42 functions as the RW control unit 60, the imaging control unit 61, the quality estimation unit 62, the estimation error derivation unit 63, and the display control unit 64 as illustrated in FIG. 4.

Figure 9:
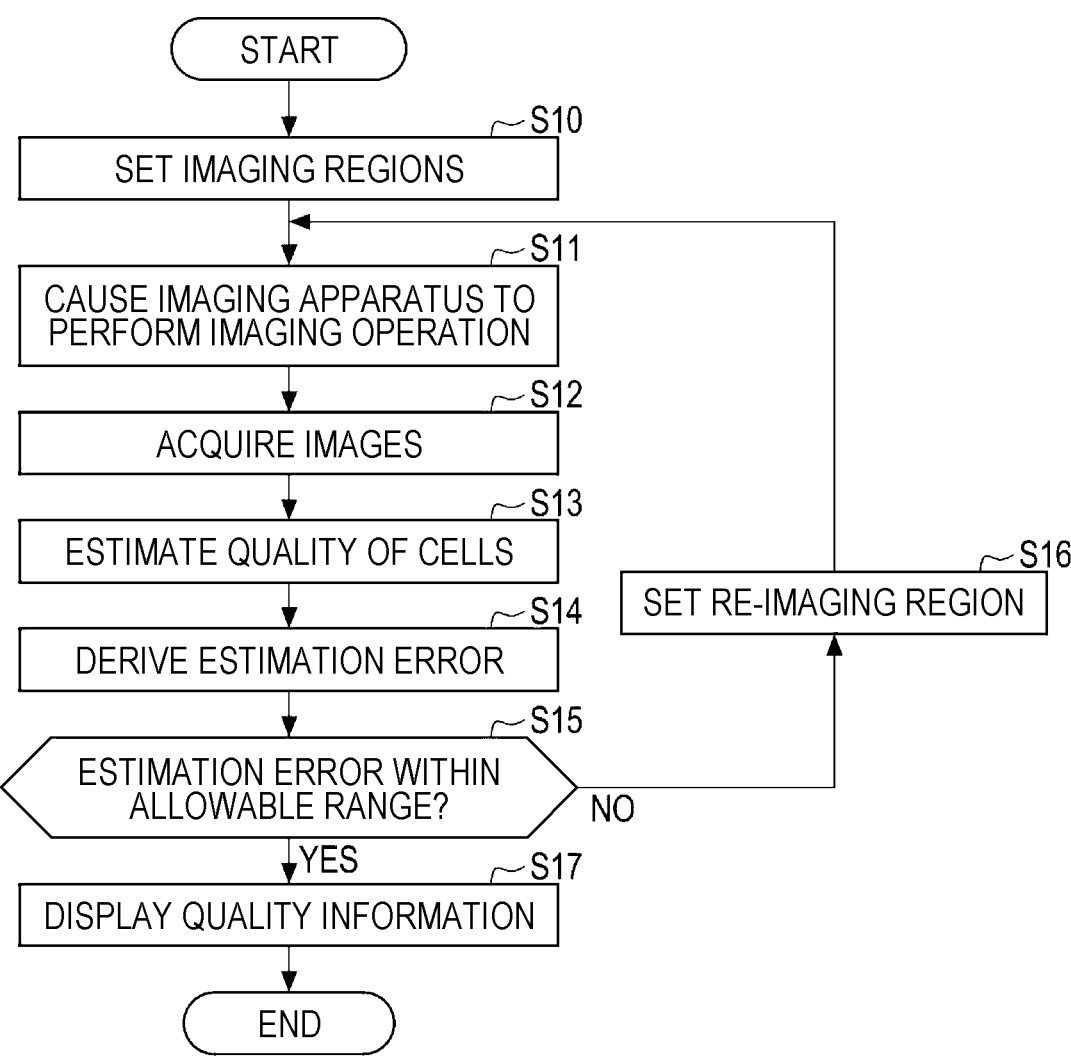
FIG. 9 is a flowchart illustrating an example of a flow of a cell quality evaluation process.

As illustrated in FIG. 9, first, the imaging control unit 61 sets the plurality of imaging regions IR in the culture region R on the basis of the imaging region information 50 (step S10). The imaging control unit 61 controls the microscope apparatus 20 to cause the imaging apparatus 23 to image the plurality of set imaging regions IR (step S11). The information processing apparatus 10 acquires the plurality of images P output from the microscope apparatus 20 as a result of the imaging apparatus 23 performing imaging (step S12).

The quality estimation unit 62 estimates the quality of cells in the above-described manner on the basis of the plurality of images P acquired from the microscope apparatus 20 (step S13). The estimation error derivation unit 63 derives the estimation error 53 of the quality of cells estimated by the quality estimation unit 62 in the above-described manner (step S14).

The imaging control unit 61 determines whether the estimation error 53 derived by the estimation error derivation unit 63 is within the allowable range (step S15). In response to determining that the estimation error 53 is out of the allowable range (step S15: NO), the imaging control unit 61 sets the re-imaging region IRS in the culture region R in the above-described manner (step S16).

After step S16 is performed, the cell quality evaluation process proceeds to step S11 again. In step S11, the imaging control unit 61 causes the imaging apparatus 23 to image the re-imaging region IRS. In subsequent step S12, the information processing apparatus 10 acquires the image P output from the microscope apparatus 20 as a result of the imaging apparatus 23 imaging the re-imaging region IRS.

In step S13, the quality estimation unit 62 adds the image P obtained by the re-imaging to the plurality of images P described above, and estimates the quality of cells. In step S14, the estimation error derivation unit 63 derives the estimation error 53 again.

In this manner, steps S11 to S16 are repeatedly performed until it is determined in step S15 that the estimation error 53 is within the allowable range. Each time re-imaging is performed, the estimation error 53 decreases.

Thereafter, if it is determined in step S15 that the estimation error 53 is within the allowable range (step S15: YES), the display control unit 64 causes the display 11 to display the quality information 52 output from the quality estimation unit 62 (step S17). The cell quality evaluation process then ends.

In the microscope observation system 2, the cell quality evaluation process illustrated in FIG. 9 is performed periodically (for example, every day) during culturing of cells.

As described above, the cell quality evaluation apparatus according to the present disclosure causes re-imaging to be performed on at least one re-imaging region in the case where the estimation error of the quality is out of the allowable range, and thus can keep the estimation accuracy of the quality at a certain level or higher with the minimum number of times of imaging. That is, the cell quality evaluation apparatus according to the present disclosure allows the quality of cells to be evaluated with a high accuracy even for a large-volume cell-culture container.

Figure 10:
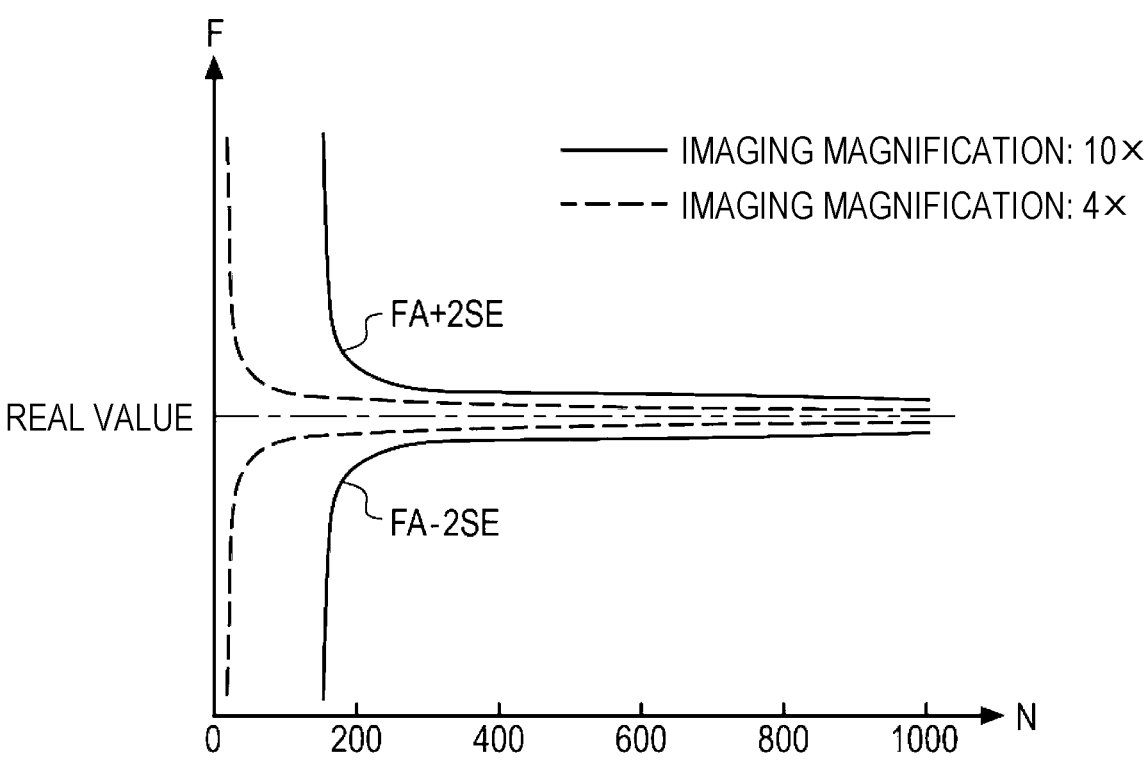
FIG. 10 is a graph illustrating the dependence of a quality estimation error on the number of captured images.

FIG. 10 illustrates the dependence of the estimation error of the quality on the number of captured images. In FIG. 10, the estimation error in the case where the imaging magnification of the imaging apparatus 23 is 10 times is compared with the estimation error in the case where the imaging magnification is 4 times. FIG. 10 illustrates an example in which the confluency is used as the feature quantity F, and a line of $\pm 2SE$ with respect to the average value FA of the feature quantities F is plotted.

As illustrated in FIG. 10, the estimation error of the quality decreases as the imaging magnification decreases, and the estimated value of the quality approaches the real value more quickly as the number of captured images N increases. This is because the size of the imaging regions IR increases as the imaging magnification decreases, and the ratio of the area of the already imaged imaging regions IR to the entirety of the cell-culture container 25 (i.e., the area ratio N/M) increases. Note that the already imaged imaging regions IR also include the re-imaging region IRS that has been subjected to re-imaging.

Modifications

Various modifications of the embodiment described above will be described below.

In the embodiment described above, in the case where re-imaging is performed, the imaging control unit 61 sets the re-imaging region IRS on the basis of the information set in advance as the imaging region information 50. However, the re-imaging region IRS may be set on the basis of a variation of the feature quantities F and the position information of the plurality of imaging regions IR. For example, the imaging control unit 61 sets the re-imaging region IRS in a region that is different from the plurality of imaging regions IR and has a large variation of the feature quantities F in the culture region R.

In addition, in the case where the feature quantity F is confluency, the imaging control unit 61 may set the re-imaging region IRS on the basis of the confluency of each of the imaging regions IR derived by the quality estimation unit 62. For example, the imaging control unit 61 sets more re-imaging regions IRS in a region with about 50% confluency than in other regions in the culture region R. That is, the imaging control unit 61 causes re-imaging to be performed more in regions with about 50% confluency than in other regions.

Figure 11:
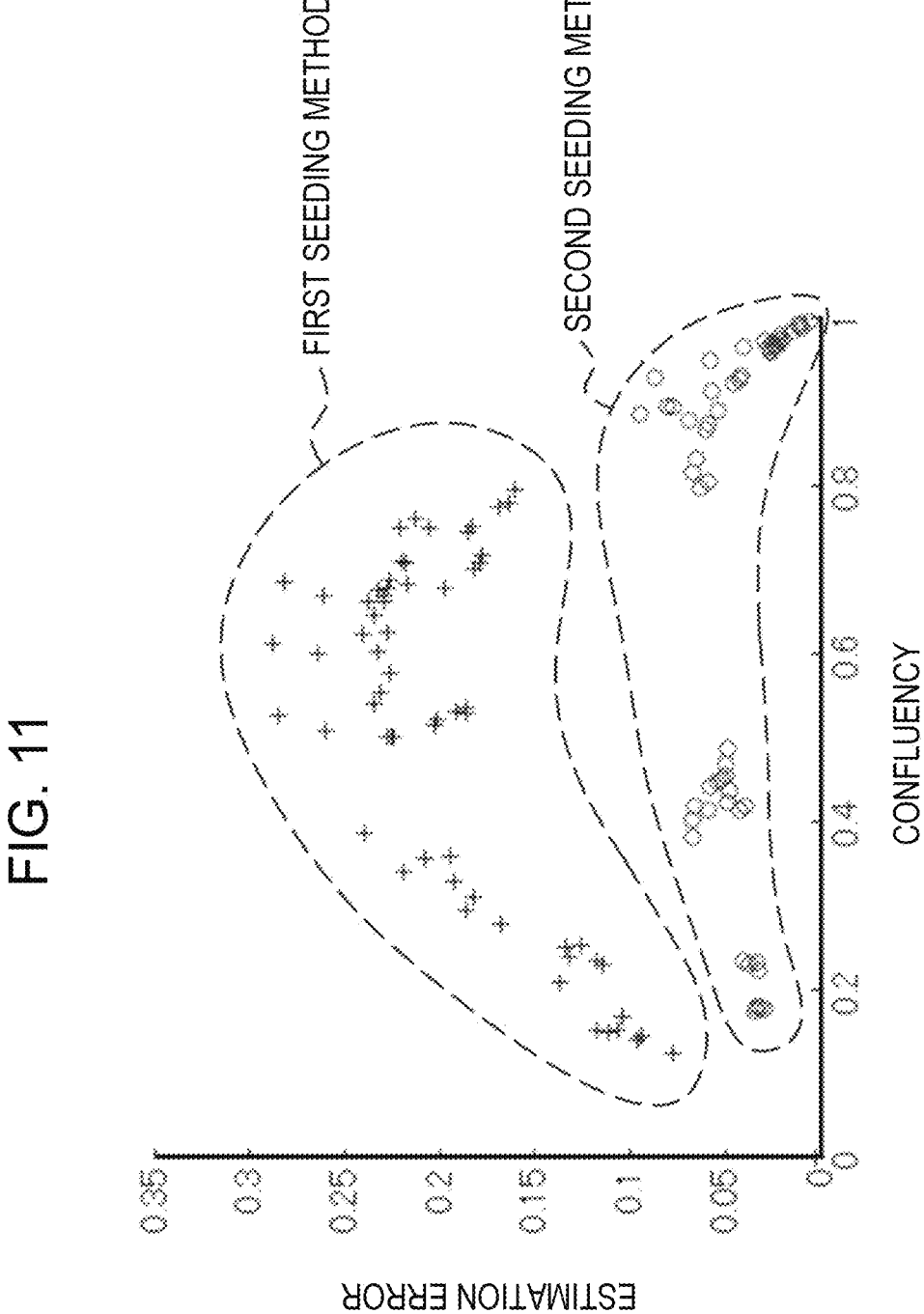
FIG. 11 is a graph illustrating a relationship between confluency and the estimation error.

FIG. 11 illustrates a relationship between the confluency and the estimation error. FIG. 11 illustrates a distribution of confluency in the case where cells are seeded using a first seeding method and a distribution of confluency in the case where cells are seeded using a second seeding method.

Figure 12A:
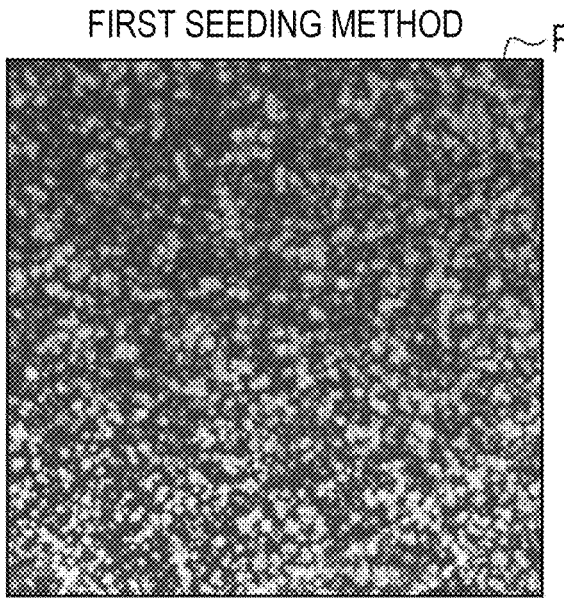
FIGS. 12A and 12B are diagrams illustrating images obtained in the cases where cells are seeded using a first seeding method and a second seeding method, specifically.
Figure 12B:
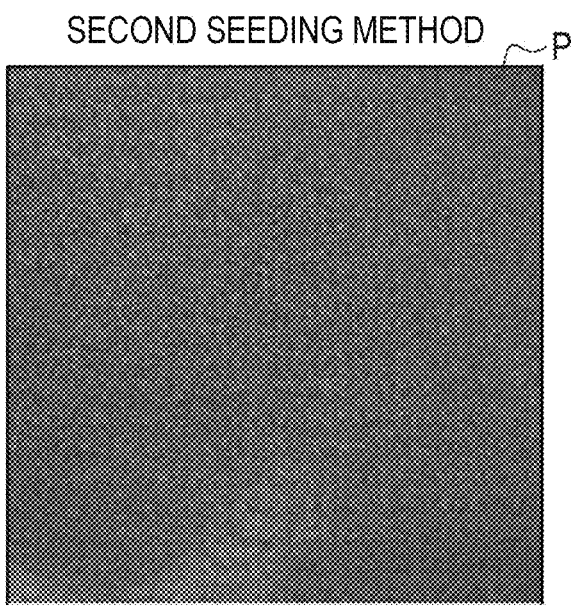

FIGS. 12A and 12B illustrate images P in the cases where cells are seeded using the first seeding method and the second seeding method. FIG. 12A illustrates an example of the image P in the case where cells are seeded using the first seeding method. FIG. 12B illustrates an example of the image P in the case where cells are seeded using the second seeding method.

FIG. 11 indicates that the estimation error of the quality increases at about 50% confluency. Performing re-imaging more in regions with about 50% confluency where the estimation error is large than in other regions can make the estimation error converge quickly.

Further, the imaging control unit 61 may set the re-imaging region IRS on the basis of a surface shape of the cell-culture container 25. This is because the distribution of the cells 30 becomes uneven depending on the surface shape of the cell-culture container 25.

Figure 13:
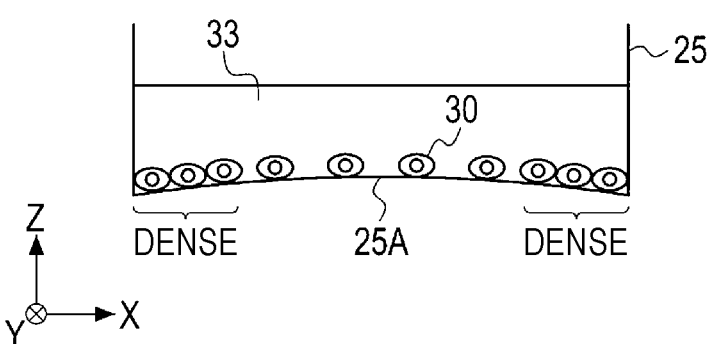
FIG. 13 is a schematic diagram illustrating an example of a cell-culture container with a curved bottom surface.

As illustrated in FIG. 13 as an example, a bottom surface (i.e., a cell adhesion surface) 25A of the cell-culture container 25 is sometimes not flat but is curved. In the example illustrated in FIG. 13, a peripheral portion of the bottom surface of the cell-culture container 25 is lower than a central portion of the cell-culture container 25. In such a case, the cells 30 are less likely to gather in the central portion of the cell-culture container 25, and are dense in the peripheral portion. That is, the confluency is low in the central portion of the cell-culture container 25 and is high in the peripheral portion. The estimation error tends to be larger in a region with lower confluency than in a region with high confluency. Thus, the imaging control unit 61 preferably sets more re-imaging regions IRS in the central portion than in the peripheral portion in the culture region R.

Figure 14:
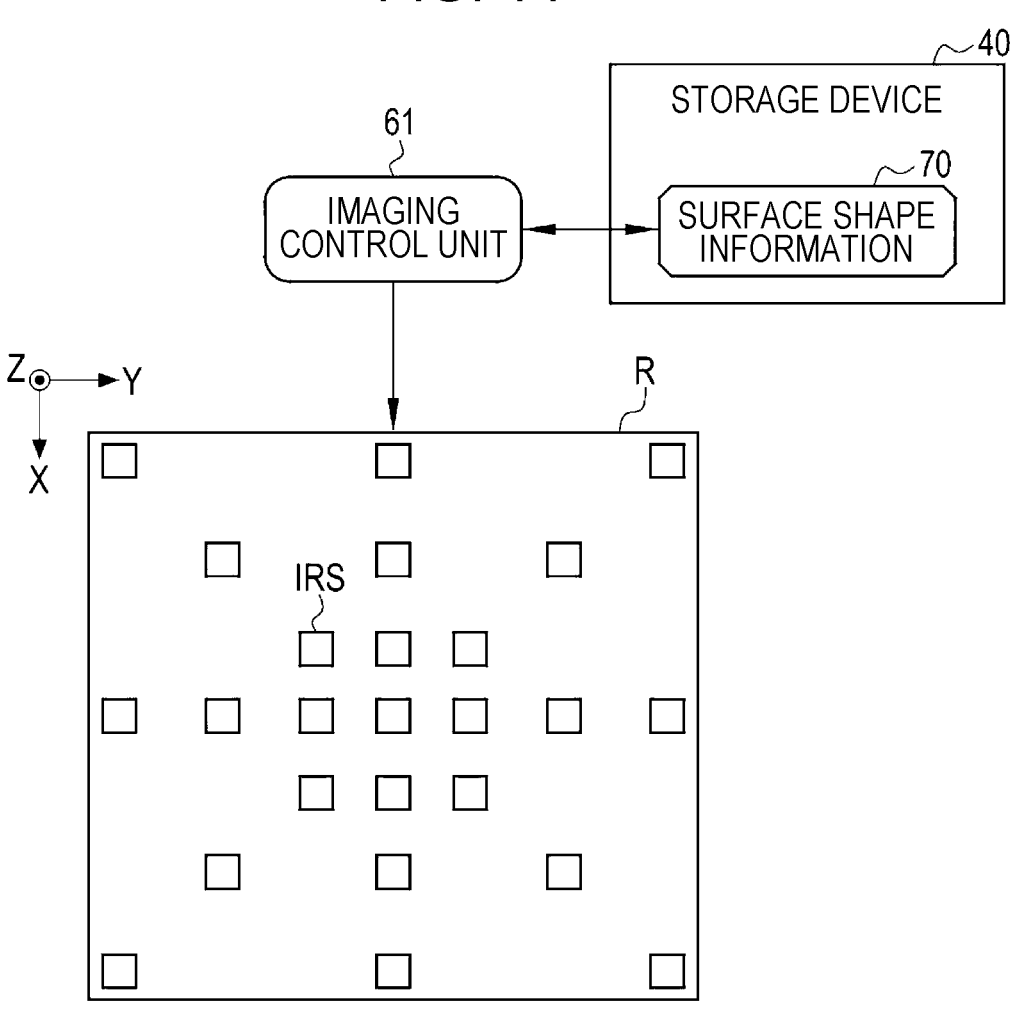
FIG. 14 is a schematic diagram illustrating an example of processing of setting re-imaging regions based on a surface shape of the cell-culture container.

FIG. 14 illustrates an example of processing of setting the re-imaging regions IRS based on the surface shape of the cell-culture container 25. In this example, the storage device 40 stores surface shape information 70 representing the shape of the bottom surface 25A of the cell-culture container 25. The imaging control unit 61 acquires the surface shape information 70 from the storage device 40, and sets the re-imaging regions IRS on the basis of the acquired surface shape information 70.

In the embodiment described above, the estimation error derivation unit 63 derives the estimation error 53 on the basis of Expressions (1) and (2) above or Expressions (1) and (3) above. However, the estimation error derivation unit 63 may derive the estimation error 53 on the basis of a table stored in advance in the storage device 40 or the like. As illustrated in FIG. 15 as an example, a table T defines a relationship between the estimation error 53 and a ratio of an area of the already imaged imaging regions IR to the entirety of the cell-culture container 25 (i.e., the area ratio N/M). Specific numerical values stored in the table T are determined by an experiment, for example. The use of such a table is useful in the case where the estimation error 53 cannot be determined using Expressions (1) and (2) above or Expressions (1) and (3) above.

In the embodiment described above, the user can input the imaging region information 50 and the allowable range information 51 in advance by using the input device 14. When the volume of the cell-culture container 25 to be used is not constant, the area of the cell-culture container 25 may be input or selected as the imaging region information 50. This allows the number of elements M of the population described above to be derived for each cell-culture container 25 to be used from the relationship between the area of the cell-culture container 25 and the area of the imaging regions IR.

In the embodiment described above, the confluency is used as the feature quantity F related to the quality of the cells 30. As an alternative to the confluency, an area of the cell nuclei 31 or an area ratio between the cell nuclei 31 and the cytoplasm 32 may be used.

The hardware configuration of the computer constituting the information processing apparatus 10 can be variously modified. For example, the information processing apparatus 10 may be constituted by a plurality of computers that are separated pieces of hardware for the purpose of increasing the processing capability and reliability.

As described above, the hardware configuration of the computer constituting the information processing apparatus 10 can be appropriately changed in accordance with the required performance such as the processing capability, the security, or the reliability. Further, not only the hardware but also the application programs such as the operation program 44 can be stored in a duplicated manner or stored in a plurality of storage devices in a distributed manner for the purpose of ensuring the security and the reliability.

In the embodiment described above, for example, various processors mentioned below can be used as a hardware structure of the processing units that perform various processes, such as the RW control unit 60, the imaging control unit 61, the quality estimation unit 62, the estimation error derivation unit 63, and the display control unit 64. The various processors include, in addition to a CPU which is a general-purpose processor that executes software (the operation program 44) to function as the various processing units, a programmable logic device (PLD), such as a field programmable gate array (FPGA), which is a processor whose circuitry is changeable after production, a dedicated electric circuit, such as an application specific integrated circuit (ASIC), which is a processor having circuitry designed specifically for executing specific processing, and the like.

A single processing unit may be constituted by one of these various processors, or by a combination of two or more processors of the same kind or different kinds (for example, a combination of a plurality of FPGAs or a combination of a CPU and an FPGA). In addition, a plurality of processing units may be constituted by a single processor.

Examples in which the plurality of processing units are constituted by a single processor include a first configuration, as exemplified by computers such as a server and a client, in which a combination of one or more CPUs and software constitutes the single processor and this processor functions as the plurality of processing units. The examples also include a second configuration, as exemplified by a system on chip (SoC) or the like, in which a processor that implements functions of the entire system including the plurality of processing units on a single integrated circuit (IC) chip is used. As described above, the various processing units are constituted using one or more of the various processors above in terms of the hardware structure.

Further, more specifically, as the hardware structure of these various processors, electric circuitry in which circuit elements such as semiconductor elements are combined can be used.

In addition, the embodiment and modifications described above can be appropriately combined within a range in which no contradiction occurs. The present disclosure encompasses, in addition to a program that causes a computer to execute the various processes, a computer-readable storage medium that stores the program in a non-transitory manner.

All the documents, patent applications, and technical standards mentioned in this specification are incorporated herein by reference to the same extent as if the individual documents, patent applications, and technical standards were specifically and individually described to be incorporated by reference.

The following technique can be grasped from the above description.

APPENDIX 1

A cell quality evaluation apparatus that evaluates a quality of cells based on a plurality of images acquired from an imaging apparatus that generates the plurality of images by imaging a plurality of imaging regions selected from entirety of a cell-culture container for culturing cells, the cell quality evaluation apparatus including:

at least one processor configured to perform a process including:

estimation processing of estimating a quality of cells in the entirety of the cell-culture container by determining feature quantities from the plurality of images and calculating an average value of the feature quantities;

derivation processing of deriving an estimation error of the quality estimated in the estimation processing, based on a variation of the feature quantities in the plurality of images and imaging information related to an area of the plurality of imaging regions; and imaging control processing of causing the imaging apparatus to perform re-imaging on at least one re-imaging region different from the plurality of imaging regions in a case where the estimation error is out of an allowable range.

APPENDIX 2

The cell quality evaluation apparatus according to Appendix 1, wherein the imaging information is a number of images that are the plurality of images, and the estimation error is represented by $\sigma/N^{1/2}$, where $\sigma$ denotes a standard deviation that is the variation of the feature quantities and N denotes the number of images.

APPENDIX 3

The cell quality evaluation apparatus according to Appendix 1 or 2, wherein in the imaging control processing, the re-imaging region is set based on the variation of the feature quantities and position information of the plurality of imaging regions.

APPENDIX 4

The cell quality evaluation apparatus according to Appendix 1 or 2, wherein in the imaging control processing, the re-imaging region is set based on a surface shape of the cell-culture container.

APPENDIX 5

The cell quality evaluation apparatus according to any one of Appendices 1 or 4, wherein the feature quantities are proportions of a cell-occupied area, areas of cell nuclei, or area ratios between cell nuclei and cytoplasm.

APPENDIX 6

The cell quality evaluation apparatus according to any one of Appendices 1 or 4, wherein
the feature quantities are proportions of a cell-occupied area, and in the imaging control processing, the imaging apparatus is caused to perform re-imaging more in a region with a proportion of a cell-occupied area of about 50% than in other regions.

APPENDIX 7

The cell quality evaluation apparatus according to any one of Appendices 1 or 6, wherein in the derivation processing, the estimation error is derived based on a table that defines a relationship between the estimation error and a ratio of an area of already imaged imaging regions to the entirety of the cell-culture container.

What is claimed is:

1. A cell quality evaluation apparatus that evaluates a quality of cells based on a plurality of images acquired from an imaging apparatus that generates the plurality of images by imaging a plurality of imaging regions selected, by the imaging apparatus, from an entirety of a cell culture region of a cell-culture container for culturing cells, the cell quality evaluation apparatus comprising:

at least one processor configured to perform a process including:

estimation processing of estimating a quality of cells in the cell-culture container by determining feature quantities from the plurality of images and calculating an average value of the feature quantities, wherein the feature quantities are proportions of a cell-occupied area, areas of cell nuclei, or area ratios between cell nuclei and cytoplasm;

derivation processing of deriving an estimation error of the quality estimated in the estimation processing, based on a variation of the feature quantities in the plurality of images and imaging information related to an area of the plurality of imaging regions, wherein the imaging information is a number N representing the total number of the generated plurality of images; and imaging control processing of causing the imaging apparatus to perform re-imaging on at least one re-imaging region of the culture region at a different position than any of the plurality of imaging regions in a case where the estimation error is out of an allowable range.

2. The cell quality evaluation apparatus according to claim 1, wherein
the estimation error is represented by $\sigma/N^{1/2}$, where $\sigma$ denotes a standard deviation that is the variation of the feature quantities.

3. The cell quality evaluation apparatus according to claim 1, wherein in the imaging control processing, the re-imaging region is set in the culture region based on the variation of the feature quantities and position information of the plurality of imaging regions.

4. The cell quality evaluation apparatus according to claim 1, wherein in the imaging control processing, the re-imaging region is set in the culture region based on a surface shape of the cell-culture container.

5. The cell quality evaluation apparatus according to claim 1, wherein
the feature quantities are proportions of a cell-occupied area, and in the imaging control processing, the at least one processor further causes the imaging apparatus to set more re-imaging regions in a first region of the culture region than in a second region of the culture region based on determining that the first region has a lower confluence than the second region and a larger estimation error than the second region.

6. The cell quality evaluation apparatus according to claim 1, wherein in the derivation processing, the estimation error is derived based on a predetermined table that defines a relationship between the estimation error and a ratio of an area of imaging regions to the entirety of the cell culture region of the cell-culture container.

7. A cell quality evaluation method for evaluating a quality of cells based on a plurality of images acquired from an imaging apparatus that generates the plurality of images by imaging a plurality of imaging regions selected, by the imaging apparatus, from an entirety of a cell culture region of a cell-culture container for culturing cells, the cell quality evaluation method comprising:

performing a process including:

estimation processing of estimating a quality of cells in the cell-culture container by determining feature quantities from the plurality of images and calculating an average value of the feature quantities, wherein the feature quantities are proportions of a cell-occupied area, areas of cell nuclei, or area ratios between cell nuclei and cytoplasm;

derivation processing of deriving an estimation error of the quality estimated in the estimation processing, based on a variation of the feature quantities in the plurality of images and imaging information related to an area of the plurality of imaging regions, wherein the imaging information is a number N representing the total number of the generated plurality of images; and imaging control processing of causing the imaging apparatus to perform re-imaging on at least one re-imaging region of the culture region at a different position than any of the plurality of imaging regions in a case where the estimation error is out of an allowable range.

8. A non-transitory computer-readable storage medium storing a program for causing a computer to execute a process for evaluating a quality of cells based on a plurality of images acquired from an imaging apparatus that generates the plurality of images by imaging a plurality of imaging regions selected, by the imaging apparatus, from an entirety of a cell culture region of a cell-culture container for culturing cells, the process comprising:

estimation processing of estimating a quality of cells in the cell-culture container by determining feature quantities from the plurality of images and calculating an average value of the feature quantities, wherein the feature quantities are proportions of a cell-occupied area, areas of cell nuclei, or area ratios between cell nuclei and cytoplasm;

derivation processing of deriving an estimation error of the quality estimated in the estimation processing, based on a variation of the feature quantities in the plurality of images and imaging information related to an area of the plurality of imaging regions, wherein the imaging information is a number N representing the total number of the generated plurality of images; and imaging control processing of causing the imaging apparatus to perform re-imaging on at least one re-imaging region of the culture region at a different position than any of the plurality of imaging regions in a case where the estimation error is out of an allowable range.

* * * * *